(12) United States Patent
Shao et al.

(10) Patent No.: US 12,116,568 B2
(45) Date of Patent: Oct. 15, 2024

(54) SHEWANELLA DECOLORATIONIS PRODUCING TETRODOTOXIN AND APPLICATION THEREOF

(71) Applicant: Yellow Sea Fisheries Research Institute, Chinese Academy of Fishery Sciences, Shandong (CN)

(72) Inventors: Changwei Shao, Shandong (CN); Sheng Du, Shandong (CN); Qian Wang, Shandong (CN); Hongyan Wang, Shandong (CN); Kaiqiang Liu, Shandong (CN); Yuyan Liu, Shandong (CN)

(73) Assignee: Yellow Sea Fisheries Research Institute, Chinese Academy of Fishery Sciences, Qingdao (CN)

( * ) Notice: Subject to any disclaimer, the term of this patent is extended or adjusted under 35 U.S.C. 154(b) by 0 days.

(21) Appl. No.: 18/518,137

(22) Filed: Nov. 22, 2023

(65) Prior Publication Data

US 2024/0200020 A1      Jun. 20, 2024

(30) Foreign Application Priority Data

Dec. 20, 2022   (CN) .......................... 202211638761.0

(51) Int. Cl.
  *C12N 1/20*         (2006.01)
  *A61K 39/00*      (2006.01)

(52) U.S. Cl.
  CPC .... *C12N 1/205* (2021.05); *A61K 2039/55544* (2013.01); *C12N 2500/72* (2013.01); *G01N 2333/195* (2013.01)

(58) Field of Classification Search
  None
  See application file for complete search history.

(56) References Cited

FOREIGN PATENT DOCUMENTS

| CN | 101993834 A | 3/2011 |
|---|---|---|
| CN | 102329849 A | 1/2012 |
| CN | 103233043 A | 8/2013 |
| CN | 105838647 A | 8/2016 |
| CN | 109593686 A | 4/2019 |
| CN | 111548969 A | 8/2020 |
| CN | 114574402 A | 6/2022 |
| CN | 114908013 A | 8/2022 |

*Primary Examiner* — S. Devi

(74) *Attorney, Agent, or Firm* — Jeenam Park

(57) ABSTRACT

Disclosed are a *Shewanella decolorationis* producing tetrodotoxin and an application thereof, falling in the field of development and utilization of medicinal microorganisms. A strain, *Shewanella decolorationis* S3-4, is deposited in the China General Microbiological Culture Collection Center (CGMCC) on Mar. 28, 2022, with a deposit number of CGMCC No. 24602. The strain can secrete a same substance as tetrodotoxin from Tetraodontidae.

1 Claim, 4 Drawing Sheets

Specification includes a Sequence Listing.

SEQUENCE LISTING

```
Sequence total quantity: 3
SEQ ID NO: 1           moltype = DNA  length = 20
FEATURE                Location/Qualifiers
source                 1..20
                       mol_type = other DNA
                       organism = synthetic construct
SEQUENCE: 1
agagtttgat cctggctcag                                              20

SEQ ID NO: 2           moltype = DNA  length = 20
FEATURE                Location/Qualifiers
source                 1..20
                       mol_type = other DNA
                       organism = synthetic construct
```

```
SEQUENCE: 2
tacgacttaa ccccaatcgc                                                    20

SEQ ID NO: 3              moltype = DNA  length = 1422
FEATURE                   Location/Qualifiers
source                    1..1422
                          mol_type = genomic DNA
                          organism = Shewanella decolorationis
SEQUENCE: 3
ggcgcgcggc tacacatgca gtcgagcggc agcacaagtg agtttactca tgaggtggcg    60
agcggcggac gggtgagtaa tgcctaggga tctgcccagt cgaggggggat aacagttgga   120
aacgactgct aataccgcat acgccctacg ggggaaagga ggggacctt tggccttccg     180
cgattggatg aacctaggtg ggattagcta gttggtgagg taatggctca ccaaggcgac   240
gatccctagc tgttctgaga ggatgatcag ccacactggg actgagacac ggcccagact   300
cctacgggag gcagcagtgg ggaatattgc acaatggggg aaaccctgat gcagccatgc   360
cgcgtgtgtg aagaaggcct tcgggttgta aagcactttc agtagggagg aaaggttgta   420
agttaatacc ttgcagctgt gacgttacct acagaagaag gaccggctaa ctccgtgcca   480
gcagccgcgg taatacggag ggtccaagcg ttaatcgaa ttactgggcg taaagcgtgc   540
gcaggcggtt tgttaagcga gatgtgaaag ccccgggctc aacctgggaa ttgcatttcg   600
aactggcaaa ctagagtctt gtagagggg gtagaattcc aggtgtagcg gtgaaatgcg   660
tagagatctg gaggaatacc ggtggcgaag gcggccccct ggacaaagac tgacgctcag   720
gcacgaaagc gtggggagca aacaggatta gatacctcgg tagtccacgc cgtaaacgat   780
gtctactcgg agtttggtgt cttgaacact gggctctcaa gctaacgcat taagtagacc   840
gcctggggag tacggccgca aggttaaaac tcaaatgaat tgacggggc ccgcacaagc    900
ggtggagcat gtggtttaat tcgatgcaac gcgaagaacc ttacctactc ttgacatcca   960
gagaactttc cagagatgga ttggtgcctt cgggaactct gagacaggtg ctgcatggct  1020
gtcgtcagct cgtgttgtga aatgttgggt taagtcccgc aacgagcgca accctatcc   1080
ttatttgcca gcgcgtaatg gcgggaactc tagggagact gccggtgata aaccggagga  1140
aggtggggac gacgtcaagt catcatggcc cttacgagta gggctacaca cgtgctacaa  1200
tggcgagtac agagggttgc aaagccgcga ggtggagcta atctcacaaa gctcgtcgta  1260
gtccggattg gagtctgcaa ctcgactcca tgaagtcgga atcgctagta atcgtgaatc  1320
agaatgtcac ggtgaatacg ttcccgggcc ttgtacacac cgcccgtcac accatgggag  1380
tgggctgcaa aagaagtggg tagcttaacc tcgggagggc gc                     1422
```

SHEWANELLA DECOLORATIONIS PRODUCING TETRODOTOXIN AND APPLICATION THEREOF

CROSS-REFERENCE TO RELATED APPLICATIONS

This application claims priority of Chinese Patent Application No. 202211638761.0, filed on Dec. 20, 2022, the entire contents of which are incorporated herein by reference.

TECHNICAL FIELD

The present disclosure relates to the field of development and utilization of medicinal microorganisms, in particular to a *Shewanella decolorationis* producing tetrodotoxin and an application thereof.

SEQUENCE LISTING

The present application contains a sequence listing which has been filed electronically in xml format and is hereby incorporated by reference in its entirety. Besides, a copy of the sequence listing in XML file is submitted, the XML copy is created on Oct. 10, 2023, is named "*SHEWANELLA DECOLORATIONIS* PRODUCING TETRODOTOXIN AND APPLICATION THEREOF-Sequence Listing" and is 5,418 bytes in size.

BACKGROUND

Tetrodotoxin (TTX) is a small molecular weight non-protein neurotoxin with short incubation period and high mortality rate. After being absorbed, tetrodotoxin quickly acts on the peripheral nerves and the central nervous system, specifically blocking voltage-gated sodium channels on cell membranes of nerve cells, disordering nerve conduction and paralyzing sensory nerves and motor nerves, and in severe cases, brainstem paralysis leads to respiratory and circulatory failure. Tetrodotoxin is contained in different tissues such as epidermis, viscus, blood, testis, ovary, liver, spleen and eyeballs of Tetraodontidae.

Because of the property of tetrodotoxin specifically blocking the voltage-gated sodium channels, tetrodotoxin can be potentially used as medicines for pain, anesthesia, detoxification, beauty and so on. TTX is often used for pain treatment, blood pressure reduction, anti-arrhythmia, local anesthesia, detoxification and tumor suppression in clinic. However, the synthetic tetrodotoxin is costly. At present, most of raw materials for extracting tetrodotoxin come from internal organs of wild Tetraodontidae, but it is difficult to be extracted due to the limited number of wild Tetraodontidae, and the killing of the wild Tetraodontidae will destroy the natural resources of Tetraodontidae.

With the in-depth study of tetrodotoxin, the "exogenous origin theory" of tetrodotoxin has been continuously confirmed. Most researchers believe that TTX in the Tetraodontidae results from the joint action of food chain and microorganisms in Tetraodontidae body. In China, it has been reported that researchers have isolated bacteria capable of producing tetrodotoxin from the liver and gonads of *Takifugu rubripes* and *Takifugu obscurus*, clearly identifying that the tetrodotoxin produced by the *Aeromonas* capable of producing tetrodotoxin isolated from the tissues of *Takifugu rubripes* and *Takifugu obscurus* is the same as the tetrodotoxin extracted from Tetraodontidae.

Although there have been studies on the microorganisms producing tetrodotoxin in China, the alternative microorganisms and cultivation method thereof are extremely limited for large-scale industrial production, which seriously limits the development of industrial production of tetrodotoxin.

SUMMARY

Aiming at the limitation of industrial production of tetrodotoxin, the present disclosure provides a *Shewanella decolorationis* S3-4 capable of producing tetrodotoxin, isolated from the liver, ovary and intestines of a wild *Takifugu ocellatus*. The *Shewanella decolorationis* S3-4 can secrete tetrodotoxin.

The present disclosure is realized by the following technical solutions.

DEPOSIT INFORMATION

A *Shewanella decolorationis* producing tetrodotoxin, a strain of S3-4, is classified as *Shewanella decolorationis* and deposited in the China General Microbiological Culture Collection Center (CGMCC) on Mar. 28, 2022 with a deposit number of CGMCC No. 24602 under the terms of the Budapest Treaty on the International recognition of the Deposit of Microorganisms for the purpose of Patent Procedure.

The present disclosure also provides a method for producing tetrodotoxin by utilizing *Shewanella decolorationis*, including the following steps: inoculating *Shewanella decolorationis* S3-4 into an LB liquid culture medium; and culturing a same at 28° C. at 200 rpm for 2-3 days.

Further, the LB liquid culture medium includes the following components: tryptone with a final concentration of 10.0 g/L, yeast extract powder with a final concentration of 5.0 g/L, and sodium chloride with a final concentration of 10.0 g/L; and the strain of *Shewanella decolorationis* S3-4 obtained by fermentation culture in the LB liquid culture medium is crushed, isolated and purified to obtain tetrodotoxin.

Compared with the related art, the present disclosure has the following beneficial effects.

The bacteria, *Shewanella decolorationis* S3-4, provided by the present disclosure can secrete the same substance as tetrodotoxin from Tetraodontidae.

DETAILED DESCRIPTION

Figure 1:
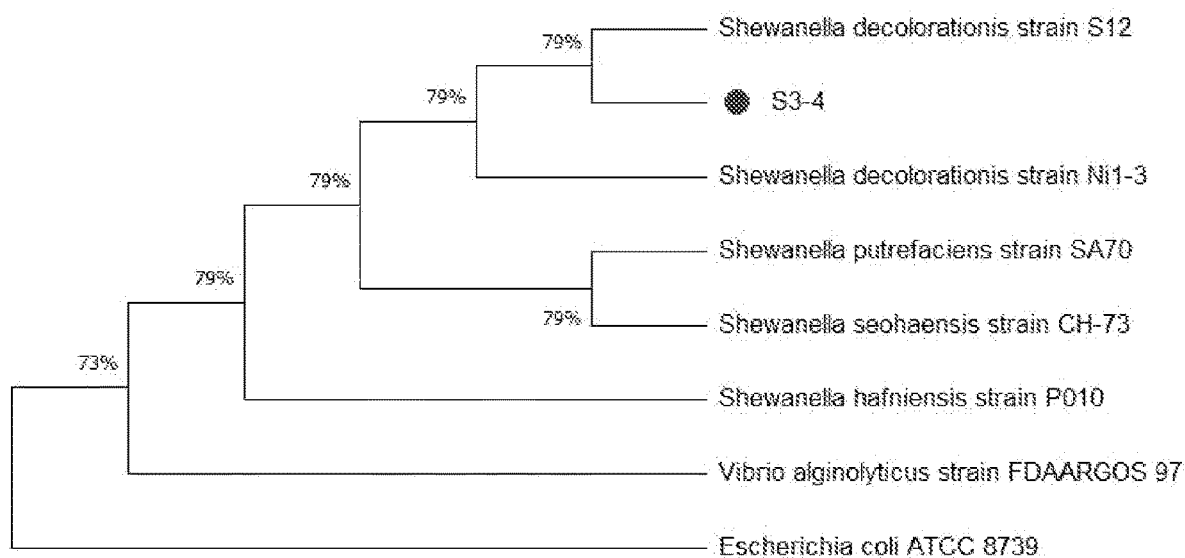
FIG. 1 is a bacterial identification diagram of a full-length 16SrDNA of *Shewanella decolorationis* S3-4 bacterium.

Technical solutions of the present disclosure will be further explained by the following examples, but the protection scope of the present disclosure is not limited by the examples in any form.

Example 1

Culture media used in the example included: 2216E solid culture media, TCBS solid culture media, LB solid culture media and LB liquid culture media, which were all commercial culture media and purchased from Qingdao Hi-tech Industrial Park Hope Bio-technology Co., Ltd.

*Takifugu ocellatus* is a small warm-water carnivorous bottom fish, which mainly inhabits nearshore waters and sometimes enters freshwater rivers and brackish-freshwater estuaries. The *Takifugu ocellatus* has an air bag, which could make its abdomen swell for self-defence when it is attacked by an enemy. The *Takifugu ocellatus* preys on small shellfish, crablat, amphipods, small crayfish and algae debris. When entering fresh water, the *Takifugu ocellatus* preys on shrimps, crabs, mussels, fry, aquatic insect larvae, angular and copepods, and occasionally aquatic vascular plants and filamentous algae. During the spawning period from April to June, fish schools migrate to the middle and lower reaches of rivers to spawn, laying demersal and viscid eggs, which belongs to one-time spawning type. The *Takifugu ocellatus* is hypertoxic in ovary and liver, non-toxic in testis, highly toxic in skins and intestines, and weakly toxic in muscle. In the present disclosure, the ovary, liver and intestines of the *Takifugu ocellatus* with strong toxicity were selected for research.

(1) A wild *Takifugu ocellatus* was selected and collected by the inventor from the estuary of Yifeng River in Shantou City, Guangdong Province. Ovarian tissues, liver and intestinal tissues of *Takifugu ocellatus* containing tetrodotoxin (TTX) were taken (2) Tissue homogenate was performed, and diluted solution was prepared with PBS at volume-mass ratios of 1:10, 1:100 and 1:1000. 100 µl of the diluted solution was taken and coated on the 2216E solid culture medium, TCBS solid culture medium and LB solid culture medium.

(3) After culturing at 28° C. for 48 hours, characteristic colonies on a plate were picked out and streaked on another 2216E solid culture medium, TCBS solid culture medium and LB solid culture medium.

(4) After culturing at 28° C. for 24 hours, an isolated single colony was streaked again for isolated culture.

(5) Streaking culture was repeated until the single colony was isolated.

The tissues in step (1) were the liver, ovary and intestines of the *Takifugu ocellatus.*

The 2216E solid culture medium included the following components: 5.0 g/L of peptone, 1.0 g/L of yeast powder, 0.1 g/L of ferric citrate, 19.45 g/L of sodium chloride, 5.98 g/L of magnesium chloride, 3.24 g/L of sodium sulfate, 1.8 g/L of calcium chloride, 0.55 g/L of potassium chloride, 0.16 g/L of sodium carbonate, 0.08 g/L of potassium bromide, 0.034 g/L of strontium chloride, 0.022 g/L of boric acid, 0.004 g/L of sodium silicate, 0.0024 g/L of sodium fluoride, 0.0016 g/L of ammonium nitrate, 0.008 g/L of disodium hydrogen phosphate and 15.0 g/L of agar.

The TCBS solid culture medium included the following components: 5.0 g/L of yeast extract powder, 10.0 g/L of peptone, 10.0 g/L of sodium thiosulfate, 10.0 g/L of sodium citrate, 5.0 g/L of Ox gallbladder powder, 3.0 g/L of natrii tauroglycocholas, 20.0 g/L of sucrose, 10.0 g/L of sodium chloride and 1.0 g/L of iron citrate, 0.04 g/L of bromothymol blue, 0.04 g/L of thymol blue and 15.0 g/L of agar.

The LB liquid culture medium included the following components: 10.0 g/L of tryptone, 5.0 g/L of yeast extract powder, 10.0 g/L of sodium chloride and 15.0 g/L of agar.

A strain was inoculated into the LB liquid culture medium, and cultured at 28° C. and 200 rpm for 2-3 days. A fermentation broth was detected by liquid chromatography-mass spectrometry, and it was found that a strain S3-4 could produce tetrodotoxin. The strain had the following morphological, physiological and biochemical characteristics.

(1) Morphological Characteristics of Bacteria

According to the conventional physiological and biochemical identification methods of bacteria, cells of *Shewanella decolorationis* were Gram-negative bacteria, with a rod-shape and a size of about (0.6-1.0)×(1.0-6.7) m, having cilia all over the body and a single polar flagellum.

(2) Main Physiological and Biochemical Characteristics

The strain had ability of facultative anaerobic growth, reducing trivalent iron, liquefying gelatin, and producing H2S. The oxidase and contact enzyme were positive, and could grow with sodium lactate, D-galactose and succinic acid as the only carbon source, but could not grow with ammonium sulfate and ammonium nitrate as the only nitrogen source.

(3) A method for identifying bacteria by a 16SrDNA full-length sequence: the DNA of the genome of the strain was obtained by extraction and isolation, 16SrDNA was amplified by PCR, and an upstream primer: 5'-agagtttgatcctggctcag-3' (SEQ ID NO. 1), a downstream primer: 5'-tacgacttaaccccaatccgc-3' (SEQ ID NO. 2), and 50 µl of a PCR reaction system were used. The PCR reaction system included: 25 µl of 2× Rapid Taq Master Mix, 1 µl of the upstream primer, 1 µl of the downstream primer, and 50 ng of the bacterial genomic DNA.

The PCR reaction program was run at 95° C. for 3 minutes; 95° C. for 15 seconds, 55° C. for 15 seconds and 72° C. for 30 seconds, totally 35 cycles; and 72° C. for 5 minutes. The amplified product of 16S rDNA full-length sequence was purified and recovered, and the recovered product was cloned in a T1 vector. *Escherichia coli* was transformed; positive clones were selected for sequencing, sequencing results were compared by BLAST N in GenBank, and the sequences with high homology were obtained. A MEGA X software was utilized for cluster analysis to determine that the isolated strain was *Shewanella decolorationis* S3-4, and the results were shown in FIG. 1. The isolated strain was *Shewanella decolorationis* S3-4.

16sDNA sequence of *Shewanella decolorationis* S3-4 were as follows (SEQ ID NO. 3).

```
ggcgcgcggctacacatgcagtcgagcggcagcacaagtgagtttactc atgaggtggcgagcggcggacgggtgagtaatgcctagggatctgccca gtcgagggggataacagttggaaacgactgctaataccgcatacgccct acgggggaaaggaggggacctttttggccttccgcgattggatgaaccta ggtgggattagctagttggtgaggtaatggctcaccaaggcgacgatcc ctagctgttctgagaggatgatcagccacactgggactgagacacggcc cagactcctacgggaggcagcagtggggaatattgcacaatgggggaaa ccctgatgcagccatgccgcgtgtgtgaagaaggccttcgggttgtaaa gcactttcagtagggaggaaaggttgtaagttaataccttgcagctgtg acgttacctacagaagaaggaccggctaactccgtgccagcagccgcgg taatacggagggtccaagcgttaatcggaattactgggcgtaaagcgtg cgcaggcggtttgttaagcgagatgtgaaagccccgggctcaacctggg aattgcatttcgaactggcaaactagagtcttgtagagggggtagaat tccaggtgtagcggtgaaatgcgtagagatctggaggaataccggtggc
```

-continued

```
gaaggcggcccctggacaaagactgacgctcaggcacgaaagcgtggg gagcaaacaggattagatacctggtagtccacgccgtaaacgatgtct actcggagtttggtgtcttgaacactgggctctcaagctaacgcattaa gtagaccgcctggggagtacggccgcaaggttaaaactcaaatgaattg acgggggcccgcacaagcggtggagcatgtggtttaattcgatgcaacg cgaagaaccttacctactcttgacatccagagaactttccagagatgga ttggtgccttcgggaactctgagacaggtgctgcatggctgtcgtcagc tcgtgttgtgaaatgttgggttaagtcccgcaacgagcgcaacccctat ccttatttgccagcgcgtaatggcgggaactctagggagactgccggtg ataaaccggaggaaggtggggacgacgtcaagtcatcatggcccttacg agtagggctacacacgtgctacaatggcgagtacagagggttgcaaagc cgcgaggtggagctaatctcacaaagctcgtcgtagtccggattggagt ctgcaactcgactccatgaagtcggaatcgctagtaatcgtgaatcaga atgtcacggtgaatacgttcccgggccttgtacacaccgcccgtcacac catgggagtgggctgcaaaagaagtgggtagcttaacctcgggagggcg c.
```

A *Shewanella decolorationis* producing tetrodotoxin, a strain of S3-4, was deposited in the China General Microbiological Culture Collection Center (CGMCC). The deposit address was No. 3, No. 1 Courtyard, Beichen West Road, Chaoyang District, Beijing. The preservation date was Mar. 28, 2022. The deposit number was CGMCC No. 24602.

Example 2

A fermentation culture method for *Shewanella decolorationis* S3-4 isolated in Example 1 included the following steps.
  (1) Bacteria were inoculated into an LB liquid culture medium.
  (2) The LB liquid culture medium was cultured at 28° C. at 200 rpm for 2-3 days.
The LB liquid culture medium included the following components: 10.0 g/L of tryptone, 5.0 g/L of yeast extract powder and 10.0 g/L of sodium chloride.

Example 3

A preparation for tetrodotoxin by utilizing the fermentation of *Shewanella decolorationis* S3-4 obtained in Example 2 included the following specific steps.

Figure 2:
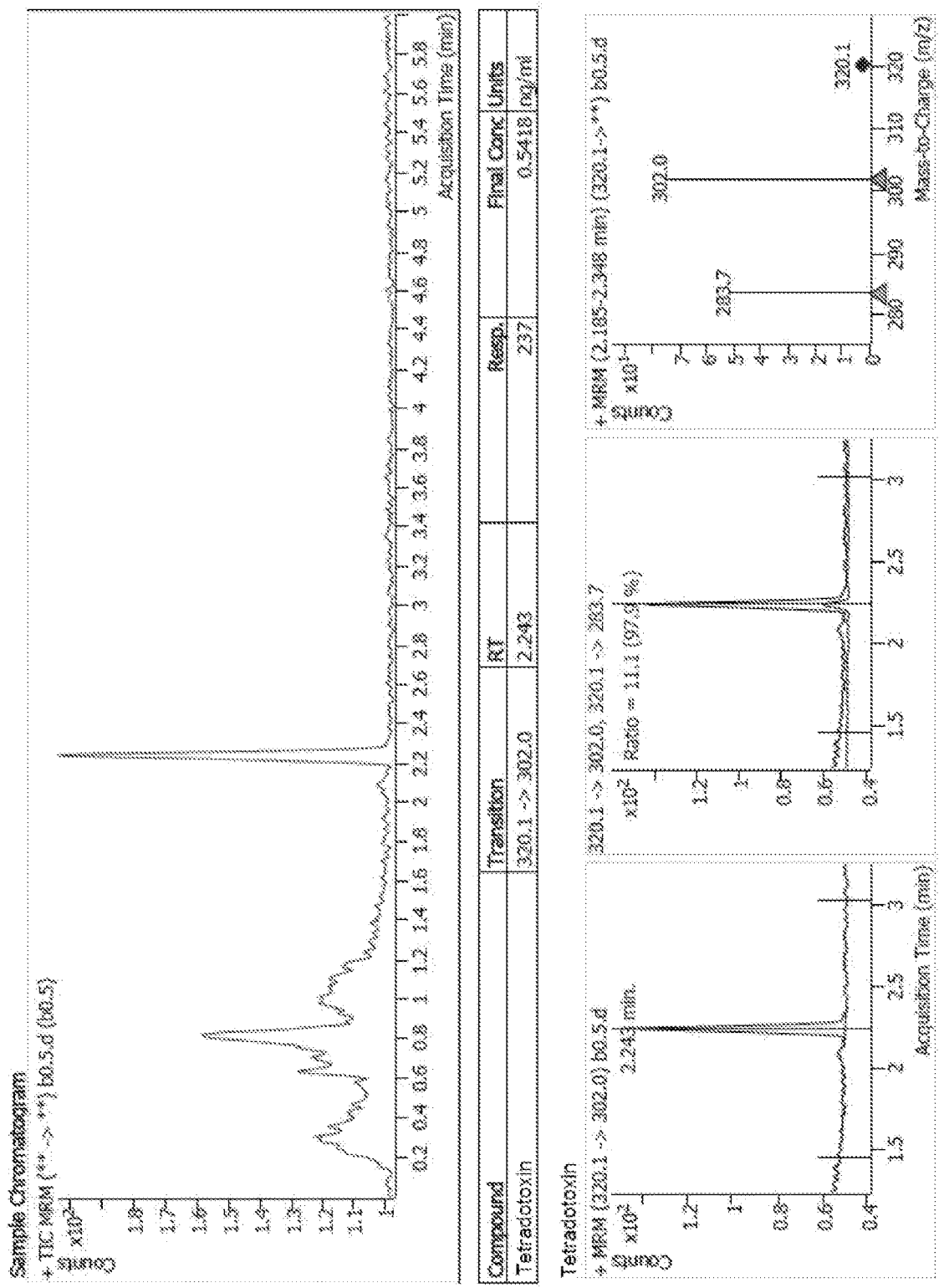
FIG. 2 is an ion chromatography-mass spectrometry diagram of a tetrodotoxin standard substance (0.5 ng/ml).
Figure 3:
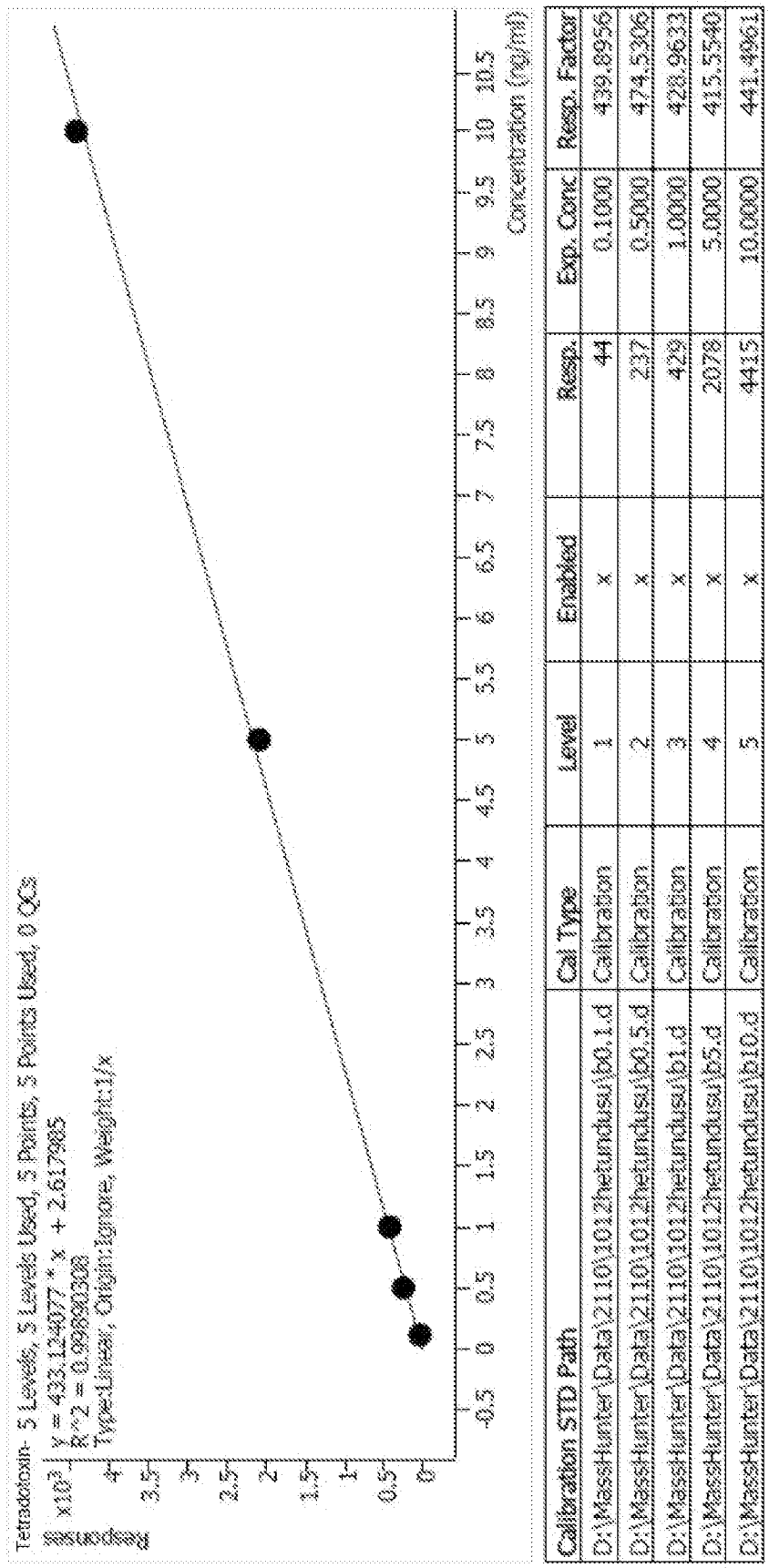
FIG. 3 is a graph of detection standard.
Figure 4:
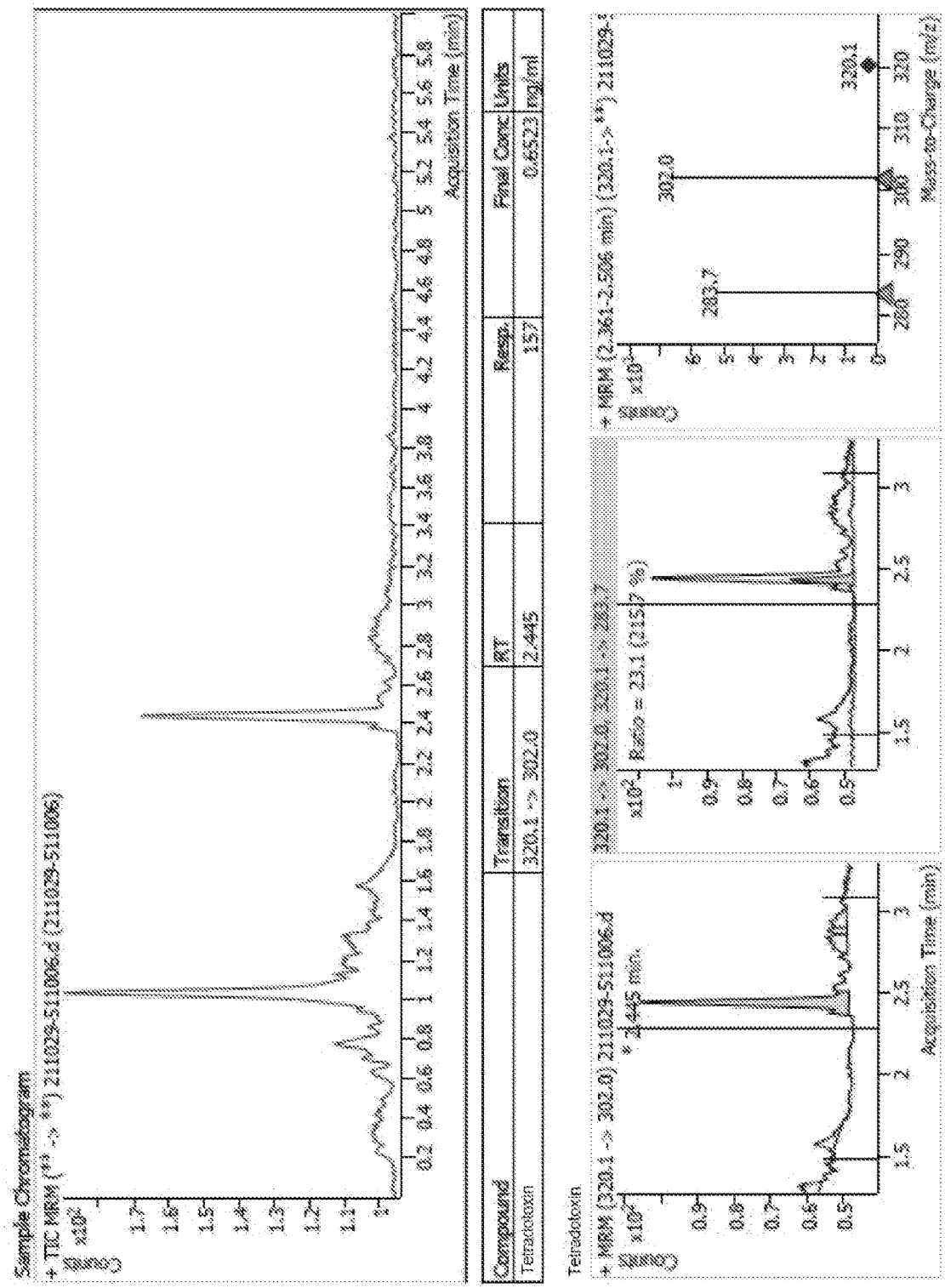
FIG. 4 is a liquid mass spectrum diagram of a bacterial source sample of *Shewanella decolorationis* S3-4.

(1) *Shewanella decolorationis* S3-4 was fermented and cultured, and then centrifuged at 4° C. at 4000×g for 30 minutes to collect strain cells.
  (2) 0.1% methanol formate was added and cells were ultrasonically crushed.
  (3) The cells were centrifuged at 8000 rpm for 5 minutes.
  (4) Supernatant was taken and filtered through an organic filter membrane with a pore size of 0.22 m.
  (5) Tetrodotoxin was detected by liquid chromatography-mass spectrometry.
  (6) Liquid chromatography-mass spectrums of a tetrodotoxin standard substance were shown in FIG. 2.
  (7) A result of a standard curve was shown in FIG. 3.
  (8) Results of liquid chromatography-mass spectrometry for the identification of *Shewanella decolorationis*-derived tetrodotoxin were shown in FIG. 4, the liquid chromatography-mass spectrometry of the *Shewanella decolorationis*-derived tetrodotoxin being consistent with that of the standard substance.

In an example of the present disclosure, bacteria were isolated from the ovary, liver and intestinal tissues of *Takifugu ocellatus*, and screened using the 2216E solid culture medium, TCBS solid culture medium and LB solid culture medium. A *Shewanella decolorationis* S3-4 capable of producing tetrodotoxin was isolated from the Tetraodontidae body for the first time, and the isolated bacteria were identified by 16S rDNA method.

The tetrodotoxin produced by the isolated *Shewanella decolorationis* S3-4 was detected by a liquid chromatography-mass spectrometry (LC-MS) method. The detection on a compound of tetrodotoxin by an LC-MS instrument is more accurate. The tetrodotoxin produced by *Shewanella decolorationis* S3-4 was determined to be a same substance as the tetrodotoxin extracted from Tetraodontidae.

According to the present disclosure, the isolated *Shewanella decolorationis* S3-4 can be cultured to isolate tetrodotoxin from bacteria on a large scale.

The basic principle, main features and advantages of the present disclosure have been shown and described above. It is to be understood by those skilled in the art that the present disclosure is not limited by the above examples, and what is described in the above examples and specifications only illustrates the principles of the present disclosure, and there will be various changes and improvements in the present disclosure without departing from the spirit and scope of the present disclosure, which fall within the scope of the claimed disclosure. The scope of protection required by the present disclosure is defined by the appended claims and equivalents thereof.

The invention claimed is:

1. A method of obtaining a tetrodotoxin of *Shewanella decolorationis* S3-4 strain deposited in the China General Microbiological Culture Collection Center (CGMCC) on 28 Mar. 2022 with the deposit number of CGMCC No. 24602, wherein the method comprises inoculating the *Shewanella decolorationis* S3-4 strain into a LB liquid culture medium and culturing at 28° C. at 200 rpm for 2-3 days, collecting cells from said culture of the *Shewanella decolorationis* S3-4 strain, and further fermentation culturing of said cells to obtain the tetrodotoxin, wherein the LB liquid culture medium comprises tryptone at a final concentration of 10.0 g/L, yeast extract powder at a final concentration of 5.0 g/L, and sodium chloride at a final concentration of 10.0 g/L, wherein the fermentation culturing comprises fermenting and culturing of the collected cells of the *Shewanella decolorationis* S3-4 strain, centrifuging at 4° C. at 4000×g for 30 minutes to obtain the fermentation cultured cells of the strain, ultrasonically crushing the fermentation cultured cells obtained by centrifugation after adding 0.1% methanol formate, centrifuging the resultant crushed cells at 8000 rpm for 5 minutes to obtain a supernatant, filtering the supernatant through an organic filter membrane with a pore size of 0.22 m, obtaining the tetrodotoxin, and subjecting the tetrodotoxin obtained to liquid chromatography-mass spectrometry to confirm that it is derived from the *Shewanella decolorationis* S3-4 strain.

* * * * *